US006333054B1

(12) United States Patent
Rogozinski

(10) Patent No.: US 6,333,054 B1
(45) Date of Patent: Dec. 25, 2001

(54) TOPICAL, NON-CYTOTOXIC, ANTIMICROBIAL HYDROGEL WITH THIXOTROPIC PROPERTIES

(75) Inventor: Wallace Rogozinski, Azusa, CA (US)

(73) Assignee: Amuchina S.p.A., Genoa (IT)

( * ) Notice: Subject to any disclaimer, the term of this patent is extended or adjusted under 35 U.S.C. 154(b) by 0 days.

(21) Appl. No.: 09/422,327

(22) Filed: Oct. 21, 1999

(51) Int. Cl.[7] .......................... A01N 59/00; A01N 59/08; A01N 25/00; C25B 1/26

(52) U.S. Cl. .................... 424/661; 205/500; 252/187.24; 252/187.25; 252/187.26; 252/187.32; 422/29; 422/37; 424/663; 424/665; 424/680; 510/370; 510/380; 514/769; 514/770; 514/949

(58) Field of Search .................................... 424/661, 663, 424/680, 665; 422/29, 37; 205/500; 510/370, 380; 252/187.24, 187.25, 187.26, 187.32; 514/769, 770, 949

(56) References Cited

U.S. PATENT DOCUMENTS

| | | | | |
|---|---|---|---|---|
| 1,813,109 | * | 7/1931 | Banks | 424/665 |
| 3,666,679 | | 5/1972 | Crotty et al. | 516/107 |
| 3,875,697 | | 4/1975 | Bracke | 47/9 |
| 4,035,483 | | 7/1977 | Bunyan | 424/665 |
| 4,125,478 | | 11/1978 | Sullivan et al. | 524/555 |
| 4,199,625 | | 4/1980 | Pilny et al. | 427/385.5 |
| 4,366,194 | | 12/1982 | Pilny et al. | 427/385.5 |
| 4,578,119 | | 3/1986 | Marcus et al. | 134/4 |
| 4,646,730 | | 3/1987 | Schonfeld et al. | 604/304 |
| 4,927,641 | | 5/1990 | Knight | 424/665 |
| 5,015,228 | | 5/1991 | Columbus et al. | 604/513 |
| 5,271,943 | | 12/1993 | Bogart et al. | 424/484 |
| 5,456,745 | | 10/1995 | Roreger et al. | 106/140.1 |
| 6,207,201 | * | 2/2001 | Placenza | 424/665 |

FOREIGN PATENT DOCUMENTS

2411748 * 3/1974 (DE) .
0 792 584 9/1997 (DE) .

OTHER PUBLICATIONS

The New Encyclopaedia Britannica, vol. 10 (15th Ed., 1994), p. 931.*

STN/CAS online, file CAPLUS, Acc. No. 1982:494767, Doc. No. 97:94767 (Mayes, Laponite–versatile inorganic colloid, Spec. Chem. (1982), vol. 2, No. 1, pp. 20–2), Abstract.*

STN/CAS online, file PROMT, Acc. No. 88:94170, ('Laporte (US):Laponite is unusual & seldom–used gelling aid for cosmetics' Drug & Cosmetic Industry, (May 1988), pp. 47, 90+), Abstract.*

STN/CAS online, file BIOSIS, Acc. No. 1983:290381, Doc. No. BA76:47873 (Pappalardo et al., 'Evaluation of a disinfectant in accordance with Swiss standards', Drugs Under Exp. Clin. Res. (1983), vol. 9, No. 2, pp. 109–114), Abstract.*

STN/CAS online, file EMBASE, Acc. No. 91279333, Doc. No. 1991279333 (Mian et al., 'Topical treatment of burn wounds with chloroxidating solution and silver sulfadiazine; A comparative study' Drugs Under Exp. Clin. Res. (1991), vol. 17, No. 4, pp. 243–252).*

PCT International Search Report, Mar. 26, 2001.

Rheological Properties of Laponite XLG, A Synthetic Purified Hectorite, J. Plaizier–Vercammen, Pharmazie, vol. 47, No. 11, Nov. 01, 1992, pp. 856–861.

* cited by examiner

*Primary Examiner*—Jose' G. Dees
*Assistant Examiner*—Frank Choi
(74) *Attorney, Agent, or Firm*—Finnegan, Henderson, Farabow, Garrett & Dunner, L.L.P.

(57) ABSTRACT

A thixotropic, non-cytotoxic, topical hydrogel that contains a proven safe and effective, broad spectrum, antimicrobial agent based on a unique electrolytically derived sodium hypochlorite solution.

16 Claims, No Drawings

TOPICAL, NON-CYTOTOXIC, ANTIMICROBIAL HYDROGEL WITH THIXOTROPIC PROPERTIES

FIELD OF THE INVENTION

This invention relates to compositions for disinfecting substrates, including tissue, and methods of disinfection. The inventive compositions comprise an electrolytic chloroxidizing agent, a viscosity-enhancing agent, an electrolyte, and water.

BACKGROUND OF THE INVENTION

Superficial topical infections are typically a consequence of a primary disease source such as chronic urinary incontinence, or are directly related to a contagious nosocomial or endemic source. Prolonged moist or wet skin conditions often lead to maceration and other changes in skin integrity which provide the opportunity for normally saprophytic bacteria and fungi to invade the site and establish an infection.

The microorganism most prevalent in the moist environment of a skin infection is *Candida albicans,* a yeast-like fungus. This type of infection is usually characterized by erythema, edema and intense pruritus. Other localized, topical infections that are bacterial in origin may be the direct result of skin-to-skin contact with a contaminated vector. One of the most serious nosocomially acquired contagious bacterial infections is methicillin resistant *Staphlococcus aureus* which is often implicated in skin cellulitis, impetigo, boils and wound infections. On occasion, the etiological agent of the infection is a combination of bacteria and fungi. This is referred to as a mixed infection, wherein dissimilar microorganisms coexist to both the benefit of and the detriment to the host.

In more serious maladies of the dermis wherein the skin is breached, especially in chronic wounds and ulcers, a variety of micro-organisms, both pathogenic and non-pathogenic, contaminate the site of the breach. Non-pathogenic microorganisms constitute the normal flora of intact skin, but these can become pathogenic when their numbers overwhelm the natural host defenses in a wound environment, and subsequently cause infection.

Quantitatively, it has been shown by Kucan et al., that open wounds can maintain a bioburden of approximately $10^5$ microorganisms per gram of tissue without the clinical manifestation of infection. "Comparisons of Silver Sulfadiazine and Physiologic Saline in the Treatment of Chronic Pressure Ulcers." *Amer. Ger. Soc.* 29:232–235, 1981. However, a bioburden of greater than $10^5$ is a significant challenge for the local wound tissue defenses. Consequently, a bioburden of $10^6$ microorganisms per gram will often result in wound infection.

Wounds that are heavily contaminated by microorganisms, but not clinically infected, are often characterized by a prolonged period of inflammation, as well as a delay in wound repair and healing. Microorganisms that contaminate wounds have been implicated as an important factor in the retardation of wound healing by interfering with leucocyte phagocytosis, and by the depletion of nutrients and oxygen required for normal tissue granulation. Ree et al., "Cutaneous Tissue Repair: Practical Implication Of Current Knowledge, Part II." *Jour. of the Amer. Academy of Dermatology* 13(6):919–941, 1985.

DESCRIPTION OF RELATED ART

Historically, wounds have been cleansed and disinfected with a host of different types of antiseptic agents ranging from acetic acid to halogen-based solutions such as complexed iodine. Topical antiseptic agents have the recognized ability to either inhibit or destroy infection producing microorganisms; however, they also induce chemical trauma and necrosis of host defense cells, such as macrophages, when used directly in the wound site (Branemark et al., "Tissue Injury Caused by Wound Disinfectants" *Bone Joint Surg. Am.* 49:48–62, 1967; Lineweaver et al., "Topical Antimicrobial Activity" *Arch. Surg.* 120:267–70 1985). Furthermore, topical antiseptic agents, which are known to be severe cytotoxins, infringe dramatically upon wound-healing processes and greatly impair the hosts' defense mechanism. Viljanto, "Disinfection of Surgical Wounds without Inhibition of Normal Wound Healing" *Arch. Surg.,* 115:253–6, 1980. Frequently, topical antimicrobials or antiseptics are used to decontaminate the intact skin site prior to surgical intervention. Antimicrobials used for this purpose are regarded as "Surgical Skin Preps" and are used in all standard protocols for skin disinfection ranging from venipuncture to major surgical procedures. Also, anti-microbials and antiseptics are routinely used as health-care personnel handwashes as a means of reducing the risk of cross-contamination.

U.S. Pat. No. 3,666,679 to Crotty relates to gelling compositions containing an anionic heteropolysaccharide biopolymer gelling agent, a linear alkyl benzene sulfonate, and various adjuvants. The gelling compositions may contain chlorine release additives such as chlorinated trisodium phosphate, chlorinated isocyanurates, sodium hypochlorite, and the like. However, such compositions require high concentrations of dilute solutions of chlorine release additives in order to achieve the desired results.

U.S. Pat. No. 4,035,483 to Bunyan is directed to antiseptic material comprising the reaction product of a protein, such as fibrin, collagen, or gelatin, and a hypochlorite. A preferred embodiment of the invention is one where the reaction product is impregnated in or coated on a sheet carrier. In another embodiment, a film is formed by reacting the hypochlorite with a substantial excess of protein. Such compositions do not possess the superior properties of the thixotropic gels.

U.S. Pat. No. 5,015,228 to Columbus et al. relates to a sterilizing device used with a needle, comprising a cover sheet and a gel medium. The preferred gel medium is a hydrogel comprising an interlaced network of agar and a copolymer of acrylamide crosslinked with the monomer N,N'-methylenebisacrylamide. Preferred sterilizing agents include sodium hypochlorite. Effective amounts of sodium hypochlorite must be highly diluted in order to achieve a desirable sterilizing effect.

Prior art chlorine-containing disinfectants are generally unsatisfactory for topical application. Common hypochlorite solutions (also called soda bleach solutions) are usually produced by bubbling chlorine in a concentrated solution of caustic soda. These bleach solutions must contain a considerable amount of sodium hydroxide in order to avoid decomposition. This gives common hypochlorite solutions a high, buffered pH as well as a corrosive nature when applied to skin or mucosa, and a cytotoxic effect upon tissue.

The common forms of topical disinfectant compositions tend to be inherently problematic. Such compositions are generally in the form of either a liquid or a gel, both of which have inherent disadvantages. Application of liquid products to intended treatment sites is difficult to control, as run-off, spillage, and poor containment are commonly encountered problems. Thick gels are not easily dispensed, and may not reach the entire surface area of wounds as easily as liquids.

SUMMARY OF THE INVENTION

It is therefore an object of this invention to overcome the problems of the prior art compositions by providing a disinfectant composition comprising an electrolytic chloroxidizing agent, a viscosity-enhancing agent, an electrolyte, and water. Such compositions are safe and effective, broad-spectrum topical antimicrobial agents and are in the form of a thixotropic, non-cytotoxic hydrogel. A related object is to provide a method for topically disinfecting a substrate, which comprises applying to said substrate an effective amount of a disinfectant composition comprising an electrolytic chloroxidizing agent, a viscosity-enhancing agent, an electrolyte, and water.

It is another object of this invention to provide a method of treating a topical infection, which comprises applying to a patient in need thereof an effective amount of a disinfectant composition comprising an electrolytic chloroxidizing agent, a viscosity-enhancing agent, an electrolyte, and water to the infected area and/or the surrounding infected area. A topical infection is understood by those of ordinary skill in the art to refer generally to a minor infection, bacterial and/or fungal in nature, which is typically superficial and localized.

It is a further object of this invention to provide a method of treating a heavily contaminated or infected wound, which comprises applying to a patient in need thereof an effective amount of a composition comprising an electrolytic chloroxidizing agent, a viscosity-enhancing agent, an electrolyte, and water to the contaminated or infected area and/or the surrounding contaminated or infected area. A heavily contaminated wound is understood by those of ordinary skill in the art to mean a wound that is heavily contaminated by micro-organisms, but not clinically infected. Such wounds are often characterized by a prolonged period of inflammation, as well as a delay in wound healing or repair. Heavily infected wounds are understood by those of ordinary skill in the art to mean wounds with a bioburden greater than $10^5$ micro-organisms per gram of tissue.

It is still a further object of this invention to provide a method of disinfecting an intact skin site prior to a surgical or invasive procedure, which comprises applying to a patient in need thereof an effective amount of a composition comprising an electrolytic chloroxidizing agent, a viscosity-enhancing agent, an electrolyte, and water Such objects can be achieved with the thixotropic hydrogels of the present invention. The rheological characteristics of thixothropy, in which the apparent viscosity decreases as the system is disturbed by stirring or shaking and then reverses during periods of dormancy, is especially useful in the administration and use of the invention described herein. The ability to apply a product to the skin with the use of simple delivery devices such as pump sprayers and squeeze tubes eliminates the characteristic disadvantages of dispensing thin liquids and thick gels, where thin liquids cannot be contained at the treatment site and permanently thick gels cannot be easily dispensed. The rheological phase shift from gel to sol to gel provides product administration latitude.

The composition is preferably in the form of a thixotropic hydrogel. The properties of the thixotropic hydrogel are imparted by the viscosity-enhancing agent. The electrolytic chloroxidizing agent comprises hypochlorite ion and hypochlorous acid, and is prepared by the partial electrolysis of a strong solution of sodium chloride in such a way as to avoid the presence of any caustic soda in the final product.

The present invention has a wide variety of uses, including the effective treatment of topical bacterial and fungal infections, the treatment of heavily contaminated or infected wounds, and the preparation of an intact skin site prior to a surgical or invasive procedure. Such uses may be realized without exhibiting the cytotoxic properties of similar antimicrobials and antiseptics.

DESCRIPTION OF THE INVENTION

This invention is directed to a topical, anti-microbial, thixotropic hydrogel prepared with varying concentrations of a viscosity-enhancing agent which imparts hydrogel consistencies that range from a heavy liquid to a thick, slightly cloudy gel. The preferred anti-microbial agent is a unique electrolytic chloroxidizer which is manufactured by the partial electrolysis of a strong solution of sodium chloride in such a way as to avoid the presence of any caustic soda in the final product.

The anti-infective properties are embodied principally in the broad-spectrum antimicrobial action of an electrolytic chloroxidizing agent, manufactured by Amuchina, S.p.A., Genova, Italy, and sold under the registered trademark Amuchina®.

The electrolytic chloroxidizer, at maximum concentration, has an active chlorine content of 11,000 ppm and forms approximately 30–40 ppm of hypochlorous acid (HOCL), also known as free available chlorine residual. Hypochlorous acid is the most effective of all chlorine residuals. The efficiency of hypochlorous acid is due to the relative ease with which it can penetrate bacterium cell walls. Due to its low molecular weight and its electrical neutrality (absence of electrical charge), the penetration of cells by hypochlorous acid is comparable to that of water. White, *Handbook of Chlorination,* Van Nostrand Reinhold Company, New York, N.Y., p. 216 (1972).

During the manufacture of the electrolytic chloroxidizer, the pH is reduced with concurrent formation of hypochlorous acid, which is nearly one-hundred (100) times more active than the hypochlorite ion in common bleach solutions. Id. at p. 223, FIGS. 4–15. Therefore, due to its lower pH and increased formation of hypochlorous acid, Amuchina® is effective at active chlorine levels substantially below those of standard sodium hypochlorite (bleach) solutions to obtain the same results. The exact mechanisms of microbiocidal action of hypochlorous acid is unclear, but as early as 1946, Green and Stump concluded that the chlorine of hypochlorous acid reacted irreversibly with the enzymatic system of bacteria, thereby killing the bacteria. Green and Stump. "The Mode of Action of Chlorine," *Jour. AWWA* 38:1301, 1946.

This anti-microbial agent is coupled with a viscosity-enhancing agent. A viscosity-enhancing agent refers to any agent that, when applied in various concentrations in an aqueous medium, results in the formation of stable hydrogels that exhibit thixotropic properties. For example, a viscosity-enhancing agent may be a clay, either natural or synthetic. In one embodiment of the invention, the hydrogel viscosity may be achieved by the use of an entirely synthetic mineral which is akin to the natural clay mineral hectorite in structure and composition. Unlike natural clay, a synthetic mineral is typically free of impurities. One such synthetic mineral is listed in the American Chemical Society's Chemical Abstracts Service (CAS) under the name of Sodium Lithium Magnesium Silicate (Reg. No. 53320-86-8) and in the Cosmetic, Toiletries and Fragrance Association (CTFA) dictionary as Sodium Magnesium Silicate. This synthetic mineral is sold commercially under the trade name Laponite®, a registered trademark of Southern Clay Products, Inc., Gonzales, Tex.

In addition to Laponite®, which is the preferred choice of a viscosity-enhancing agent for the present invention, certain semi-synthetic and naturally occurring clay minerals, including mixtures thereof, are useful in the present art. The following clay minerals, classified by structure, may also be used according to the invention:

I. Amorphous
 Allophane group
II. Crystalline
 A) Two-layer type (sheet structures composed of units of one layer of silica and one layer of alumina octahedrons)
  1. Equidimensional Crystals
   Kaolinite Group
   Kaolinite, Nacarite
  2. Elongate Crystals
   Halloysites
 B) Three-layer types (sheet structures composed of two layers of silica tetrahedrous and one central dioctahedral or trioctahedral layer. Montmorillonite, sauconite, vermiculite, nontronite, saponite, hectorite, bentonite.
 C) Chain structure types (hornblende like chains of silica tetrahedrons linked together by octahedral groups of oxygen and hydroxyls containing Al and Mg atoms) attapulgite, sepiolite and palygorskite.

The swelling properties of these natural clay minerals permit colloidal particles to form upon hydration. These colloidal particles exhibit repulsive electrical surface charges, which are able to maintain a uniform suspension in solution. With the addition of an ionic compound (e.g., sodium chloride, potassium chloride, etc.) to the colloidal suspension, the repulsive particle charges are reduced significantly allowing the formation of a gel with rheological characteristics that are typical of the clay mineral used. The formed gel demonstrates flow properties and Theological behavior classically termed thixotropic, wherein a semi-solid gel can be induced by shaking or stirring, to become a sol (a thin liquid) and revert once again to a semi-solid gel upon standing.

In another embodiment, organic modifiers and clay mineral viscosity-enhancing agents may be combined in order to realize the best properties of both. When used in combination with an approximate ratio of 4 parts clay mineral to 1 part organic modifier, the clay and the organic modifier may be combined to provide a viscosity-enhancing agent. Organic modifiers are generally cellulosic in nature, and are typically used in the art to form non-thixotropic gels. Non-limiting examples of such organic modifiers include hydroxypropyl methyl cellulose, guar hydroxypropyl trimonium chloride, carbomer, xanthan gum, and polyvinylpyrrolidone.

Sodium chloride is the preferred electrolyte in this embodiment. Other compounds, including alkali metal and alkali earth metal salts, that disassociate into electrolytes such as the salts of potassium, magnesium and calcium can also be used to initiate ionic bonding in the formation of thixotropic gels. Alternative electrolytes produce gels with properties equivalent to those utilizing sodium chloride. In a disinfectant composition comprising an electrolytic chloroxidizing agent, a viscosity-enhancing agent, an electrolyte, and water, the electrolyte is present in an amount of from about 0.01 to about 10% by weight of the composition.

According to one embodiment of the invention, in the disinfectant compositions according to the present invention, the electrolytic chloroxidizing agent has an active chlorine content of from about 100 to about 11,000 ppm. Active chlorine content refers to the amount, in parts per million, of free chlorine ions in solution.

According to another embodiment, in the disinfectant compositions according to the present invention, the electrolytic chloroxidizing agent has an active chlorine content of from about 200 to about 1100 ppm.

According to a preferred embodiment, in the disinfectant compositions according to the present invention, the concentrated electrolytic chloroxidizer solution is diluted from 11,000 ppm to provide a free chlorine content of about 500 to about 825 ppm.

According to another preferred embodiment, in the disinfectant compositions according to the present invention, the concentrated electrolytic chloroxidizer solution is diluted from 11,000 ppm to provide a free chlorine content of about 550 to about 825 ppm. This concentration has been shown to be effective against a wide range of pathogenic species of bacteria, fungi and viruses.

The process of diluting the full-strength (11,000 ppm active chlorine) electrolytic chloroxidizer is routine to those of ordinary skill in the art. For example, 98 parts deionized water is combined with 2 parts electrolytic chloroxidizer to yield a disinfectant composition having 220 ppm active chlorine; 95 parts deionized water is combined with 5 parts electrolytic chloroxidizer to yield a disinfectant composition having 550 ppm active chlorine; and 90 parts deionized water is combined with 10 parts electrolytic chloroxidizer to yield a disinfectant composition having 1100 ppm active chlorine.

The dilute electrolytic chloroxidizer solution is then combined with the hectorite viscosity enhancing agent, water and sodium chloride, to produce a sol that coagulates to a gel when left standing undisturbed, but which quickly liquefies again when agitated by stirring or vibration. For clay suspensions with negatively charged micelles (electrically charged colloidal particles), the hydroxides and halides of lithium and sodium produce the typical thixotropic systems. Laponite®, with its clay type structure, will segregate into numerous tiny platelets and align together with ionic bonds to form a thixotropic architecture. Upon dispersion of Laponite® in deionized water, an electrical double layer develops around the platelets, resulting in an electrical repulsion between platelets so that the system remains in a static sol state. Subsequent additions of electrolyte, such as sodium chloride or the antimicrobial electrolytic chloroxidizer, cause the double electrical layer surrounding the platelets to weaken thereby allowing electrostatic and Van der Waals attractive forces to dominate and the system to develop ionic bonds which fosters the transition from the sol to the gel state.

In accordance with an embodiment of the present invention, an electrolytic chloroxidizer is used which is composed of hypochlorite ion (OCL) and hypochlorous acid (HOCL) at a concentration of from about 0.022% to about 0.11% w/w, which constitutes the available chlorine of the broad spectrum antimicrobial agent. A thixotropic, viscosity-enhancing agent conforming to the empirical formula $Na_{0.7+}[(Si_8Mg_{5.5}Li_{0.3})O_{20}(OH_4)]^{0.7}$ is used in a concentration of 0.1% to 10% w/w and serves as the gel matrix once ionic bonding has been completed. In a preferred embodiment a high purity U.S.P. grade of sodium chloride which conforms to the empirical formula, NaCl, and comprises from 0.1% to 10% w/w is added. The sodium chloride acts to initiate ionic bonding between the hectorite micelle platelets of the thixotropic viscosity enhancing agent.

The disinfectant compositions according to the invention may be used for topically disinfecting a substrate, which comprises applying to said substrate an effective amount of a disinfectant composition comprising an electrolytic chloroxidizing agent, a viscosity-enhancing agent, an electrolyte, and water.

The disinfectant compositions according to the invention may also be used in a method for the treating a topical infection, which comprises applying to a patient in need thereof an effective amount of said disinfectant composition to the infected area and/or the surrounding infected area.

The disinfectant compositions according to the invention may additionally be used in a method of treating a heavily contaminated or infected wound, which comprises applying to a patient in need thereof an effective amount of said disinfectant composition to the contaminated or infected area and/or the surrounding contaminated or infected area.

Additionally, the disinfectant compositions according to the present claims may be used in a method for disinfecting an intact skin site prior to a surgical or invasive procedure, which comprises applying to a patient in need thereof an effective amount of a composition comprising an electrolytic chloroxidizing agent, a viscosity-enhancing agent, an electrolyte, and water

EXAMPLE

Manufacturing Method for Thixotropic Hydrogel (1) From about 0.1% to about 10% w/w Laponite®, dependent upon the desired final viscosity, is slowly dispersed into a suitably sized vessel containing U.S.P. deionized water under continuous high shear, high speed mixing. The mixing is continued until the Laponite® is fully hydrated and the solution appears clear.

(2) From about 2% to about 10% w/w of full strength electrolytic chloroxidizer (11,000 ppm active chlorine), dependent upon the desired concentration of active chlorine in the final product, is slowly added to the mixture in step (1) under continuous high shear, high speed mixing. Viscosity of the mixture will increase significantly. High shear, high speed mixing is continued until the solution appears clear.

(3) From about 0.1% to about 10% w/w of a U.S.P. grade sodium chloride, dependent upon the concentration of Laponite® in the mixture in step (1), is added to the mixture in step (2) under continuous high shear, high speed mixing. Viscosity of the mixture increases dramatically.

The resulting composition exhibits excellent thixotropic properties. It is a semi-solid gel upon standing, but upon shaking or stirring it becomes a thin liquid. Left to stand, it again reverts to a semi-solid gel.

What is claimed is:

1. A thixotropic hydrogel disinfectant composition comprising:

(A) an electrolytic chloroxidizing agent which:

(i) is prepared by the partial electrolysis of a sodium chloride solution, wherein pH is reduced with a concurrent formation of hypochlorous acid;

(ii) comprises hypochlorite ion and hypochlorous acid; and (iii) provides an active chlorine content ranging from about 100 to about 11,000 ppm;

(B) a viscosity-enhancing agent comprising a natural or synthetic clay;

(C) an electrolyte; and (D) water.

2. The composition according to claim 1, wherein said clay is a synthetic clay.

3. The composition according to claim 2, wherein said synthetic clay has the following formula:

$$Na_{0.7}[(Si_8Mg_{5.5}Li_{0.3})O_{20}(OH_4)]_{0.7}.$$

4. The composition according to claim 2, wherein said synthetic clay of the formula

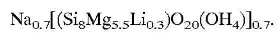

$$Na_{0.7}[(Si_8Mg_{5.5}Li_{0.3})O_{20}(OH_4)]_{0.7}.$$

is present in an amount of from about 0.1 to about 10% by weight of the composition.

5. The composition according to claim 1, wherein said viscosity-enhancing agent further comprises an organic modifier.

6. The composition according to claim 1, wherein said electrolyte is present in an amount of from about 0.1 to about 10% by weight of the composition.

7. The composition according to claim 6, wherein said electrolyte is sodium chloride.

8. The composition according to claim 1, wherein said electrolytic chloroxidizing agent has an active chlorine content of from about 200 to about 1100 ppm.

9. The composition according to claim 1, wherein (A) the electrolytic chloroxidizing agent is present in an amount which provides an active chlorine content of from about 200 to about 1100 ppm;

(B) the viscosity enhancing agent is a synthetic sodium lithium magnesium silicate, and is present in an amount of from about 0.1 to about 10% by weight;

(C) the electrolyte is sodium chloride, and is present in an amount of from about 0.1 to about 10% by weight; and the balance of the composition comprises water.

10. A method of topically disinfecting a substrate, which comprises applying to said substrate an effective amount of the composition according to claim 1.

11. The method according to claim 10, wherein said substrate is skin.

12. The method according to claim 10, wherein said substrate is a wound.

13. A method of treating a topical infection, which comprises applying to a patient in need thereof an effective amount of the composition according to claim 1 to the infected area and/or the surrounding infected area.

14. A method of treating a heavily contaminated or infected wound, which comprises applying to a patient in need thereof an effective amount of the composition according to claim 1 to the contaminated or infected area and/or the surrounding contaminated or infected area.

15. A method of disinfecting an intact skin site prior to a surgical or invasive procedure, which comprises applying to a patient in need thereof an effective amount of a composition according to claim 1.

16. A thixotropic hydrogel disinfectant composition comprising:

(A) an electrolytic chloroxidizing agent which:

(i) is prepared by the partial electrolysis of a sodium chloride solution, wherein pH is reduced with a concurrent formation of hypochlorous acid;

(ii) comprises hypochlorite ion and hypochlorous acid; and (iii) provides about 11 g of active chlorine per liter of solution;

(B) a viscosity-enhancing agent comprising a natural or synthetic clay;

(C) an electrolyte; and (D) water.

* * * * *